United States Patent
Howell

(10) Patent No.: US 10,827,701 B1
(45) Date of Patent: Nov. 10, 2020

(54) ***BUGLOSSOIDES ARVENSIS* 'SHANNON'**

(71) Applicant: Philip Howell, Cambridge (GB)

(72) Inventor: Philip Howell, Cambridge (GB)

(73) Assignee: NIAB Trading Ltd. (GB)

( * ) Notice: Subject to any disclaimer, the term of this patent is extended or adjusted under 35 U.S.C. 154(b) by 0 days.

(21) Appl. No.: 16/694,880

(22) Filed: Nov. 25, 2019

(51) Int. Cl.
*A01H 6/00* (2018.01)
*A01H 5/10* (2018.01)

(52) U.S. Cl.
CPC ............... *A01H 5/10* (2013.01); *A01H 6/00* (2018.05)

(58) Field of Classification Search
CPC ........................................................ A01H 6/00
See application file for complete search history.

(56) References Cited

U.S. PATENT DOCUMENTS 9,648,831 B2 * 5/2017 Howell .................... A01H 5/10

* cited by examiner

*Primary Examiner* — David H Kruse
(74) *Attorney, Agent, or Firm* — Cassandra Bright

(57) ABSTRACT

A new and distinct *Buglossoides arvensis* plant named 'Shannon' characterized by narrow plant growth and abundant side shoot development. Seeds are distinctively well retained on the plant. Plants flower March to June and require vernalization to induce flowering. Seed germination rate is typically 80%. Seeds of the plant are used in the production of the oil commercially known Ahiflower oil.

5 Claims, 1 Drawing Sheet
(1 of 1 Drawing Sheet(s) Filed in Color)

BUGLOSSOIDES ARVENSIS 'SHANNON'

FIELD OF THE INVENTION

The present invention relates to a new, distinct and stable hybrid of *Buglossoides arvensis*, hereinafter referred it as 'Shannon'. The present invention relates to seeds which are the *Buglossoides arvensis* 'Shannon', as well as, plants and the plant parts produced by these seeds which have all the morphological and physiological characteristics of the *Buglossoides arvensis* 'Shannon'. The present invention also relates to methods for producing these seeds and plants of the *Buglossoides arvensis* 'Shannon'. Furthermore, the present invention relates to method of producing progeny *Buglossoides* plants by crossing *Buglossoides* 'Shannon', as either the female or seed or male or pollen parent, with another *Buglossoides* plant and selecting progeny.

BACKGROUND OF THE INVENTION

The present invention relates to a new, distinct and stable variety of *Buglossoides arvensis*, and hereinafter referred to by the variety denomination 'SHANNON'. The new *Buglossoides* 'Shannon' originated from the process of selection of wild collected seed, which was germinated, observed selected and subsequently self-pollinated. Germination, selection and self-crossing were made as part of a controlled breeding program by the inventor at a research greenhouse and outdoor field facility in Cambridge, England. The new variety was initially selected June 2013. The selected seed line was first multiplied in pots and an outdoor field in November 2013 Cambridge, England.

*Buglossoides* is a member of the Boraginaceae family. *Buglossoides* is a genus consisting of 15 species of annual or perennial herbs, native to Europe and Asia. They grow naturally in habitats ranging from sunny scrub to rocky slopes and woodland areas.

*Buglossoides* has been identified as a potentially interesting commercial crop for seed production, with the seeds useful for oil production. The oil derived from *Buglossoides* trades under the commercial name Ahiflower oil. Research has shown that vegetable oils containing stearidonic acid (SDA) could be a dietary source of n-3 fatty acids that would be more effective in increasing tissue eicosapentaenoic acid (EPA) concentrations than are current alpha linolenic acid (ALA) containing vegetable oils. The use of SDA-containing oils in food manufacture could provide a wide range of dietary alternatives for increasing tissue EPA concentrations. Ahiflower oil is indicated to be a more efficient omega-3 alternative to flax, chia, and other ALA-rich dietary oils.

Seeds of *Buglossoides* have been approved for the above mentioned use by the FDA.

*Buglossoides* can be propagated by vegetative, asexual practices. However, this method is impractical for commercial field purposes.

Methods for cultivation and crossing of *Buglossoides* are not well known. However, it is known some varieties are suitable for Winter production, requiring vernalization, whereas some varieties will not require vernalization and produce seeds during the Summer season from Spring planting.

*Buglossoides arvensis* plants are known to produce seeds prolifically. To produce a commercial crop, it has been necessary to address the issue of variety stability, as well as seed dormancy. The inventor has developed a new variety which can be self-pollinated and reproduced true to try from seed. Plants produced by this method are uniform with respect their morphological and physiological characteristics.

A need exists for a greater variety of *Buglossoides* cultivars for commercial seed production, under a variety of environmental conditions. Additionally, a need exists for additional *Buglossoides arvensis* cultivars that can be easily propagated by seed, with consistent results. The new *Buglossoides* Shannon was developed through a controlled breeding program and exhibits unique, desirable and stable characteristics.

SUMMARY OF THE INVENTION

The present invention provides *Buglossoides* plant selections that can be planted in the Winter, requiring vernalization to produce seeds during Summer. Additionally, plants of 'Shannon' typically produce many side shoots, with these side shoots starting to emerge at a lower section of the main stem than typical of *Buglossoides*. Plants begin flowering uniquely early. Germination rate of the new variety is typically around 80%, much higher than typical for *Buglossoides*. Plants are cold hardy, with improved Autumnal survival rate, observed to tolerate temperatures as low as −5° C. Additionally, plants have a superior quality to retain seeds on the plant. Agronomic performance and oil content are consistent and desirable for commercial purposes. These qualities distinguish the new cultivar from typical *Buglossoides arvensis* varieties.

These and other objectives have been achieved in accordance with the present invention which provides ' Shannon' as a new *Buglossoides* cultivar that is a product of a planned breeding program conducted by the inventor Philip Howell, in Cambridge, England.

The new variety 'Shannon' can be produced by sexual reproduction by to produce a population of progeny plants, each of which has the combination of characteristics as herein disclosed for the new variety 'Shannon'.

2500 seeds of variety 'Shannon' were deposited and accepted on Jan. 30, 2020 at the National Collection of Industrial Food and Marine Bacteria (NCIMB), Ferguson Building, Bucksburn, Aberdeen, Scotland, a Budapest Treaty recognized depository which affords permanence of the deposit, and accorded International Depository Authority Accession No. NCIMB-43565.

OBJECTS OF THE INVENTION

The present invention relates to seeds which produce *Buglossoides arvensis* 'Shannon'. The present invention also relates to *Buglossoides* plants, and parts thereof, having all the physiological and morphological characteristics of *Buglossoides arvensis* 'Shannon'. The present invention relates to a plant produced from seeds which are *Buglossoides arvensis* 'Shannon'. The present invention also relates to plant parts, such as pollen, seeds or inflorescence produced by *Buglossoides arvensis* 'Shannon'.

The present invention relates to a method of producing seed which are *Buglossoides arvensis* 'Shannon'.

The present invention also relates to a method of producing plants having all the physiological and morphological characteristics of the *Buglossoides arvensis* 'Shannon' comprising the steps of (a) self-pollinating *Buglossoides arvensis* 'Shannon' a (b) harvesting seeds produced from said cross; and (c) producing plants from said harvested seeds.

The present invention also relates to producing progeny plants from the cross of *Buglossoides arvensis* 'Shannon', as the female or male parent, with another *Buglossoides* plant, and selecting progeny plants from this cross.

BRIEF DESCRIPTION OF THE PHOTOGRAPH

The patent or application file contains one drawing executed in color. Copies of this patent or patent application publication with color drawings will be provided by the Office upon request and payment of the necessary fees.

The accompanying photographs illustrate the overall appearance of the new *Buglossoides arvensis* 'Shannon' showing the colors as true as is reasonably possible with colored reproductions of this type. Colors in the photograph may differ slightly from the color values cited in the detailed botanical description which accurately describes the color of 'Shannon'.

The FIGURE shows two plants of *Buglossoides arvensis* grown outdoors during Winter and Spring months. The plant on the right is the variety 'Shannon'. The plants on the left is the variety 'Portland', filed concurrently.

DETAILED BOTANICAL DESCRIPTION

The present invention was created by the inventor, Philip Howell in Cambridge, England.

This invention is directed to a *Buglossoides arvensis* plant having all the morphological and physiological characteristics of the variety 'Shannon' produced from seeds The new *Buglossoides arvensis* 'Shannon' can also be produced by asexually reproducing progeny. Asexual reproduction of the new cultivar by vegetative means by cuttings was first performed in 2010, in Cambridge, England. The first 'Shannon' plants propagated through the use of such cuttings are maintained in Cambridge, England and have reproduced at least 5 generations. Subsequent asexual reproduction has demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'Shannon' which in combination distinguish this *Buglossoides* as a new and distinct cultivar:
1. Many side shoots (starting from lower down the main stem).
2. Large seed (TSW typically 5.0 g).
3. Good germination rate—typically 80%.
4. Good seed retention on plant.
5. Good autumn survival (survives −5° C.).
6. Narrow plant form.

Of the few commercial cultivars known to the present inventor, the most similar in comparison to the new *Buglossoides arvensis* 'Shannon' is the unnamed, unpatented *Buglossoides arvensis* maintained at Kew Gardens, hereafter referred to as 'FitzRoy', U.S. Pat. No. 9,648,831. 'Shannon' differ from plants of 'FitzRoy' in the following:
1. 'Shannon' stands taller in the field.
2. 'Shannon' produces more side shoots per plant.
3. 'Shannon' bears larger seed (TSW 5.0 g versus 'FitzRoy' 2.4 g).
4. 'Shannon' shows better resistance to powdery mildew, especially later in the season.

'Shannon' can also be compared to a *Buglossoides arvensis* 'Malin', U.S. Pat. No. 9,439,379. Plants of 'Malin' differ from plants of 'Shannon' in the following:
1. 'Shannon' is a winter type and requires vernalisation to initiate flowering.
2. From equivalent autumn sowings, 'Shannon' gives a higher plant population coming into spring.
3. 'Shannon' shows much better seed retention at full crop maturity.

'Shannon' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter; quantity of seeds produced can occur, depending upon environmental conditions and planting density.

The aforementioned photographs, together with the following observations, measurements and values describe the new *Buglossoides* 'Shannon' as grown outdoors in Hertfordshire, England. Plants of 'Shannon' were grown outdoors in a research field with temperatures ranging from approximately 5° C. to 18° C. during the day and night temperatures ranging from −2° C. to 7° C. No artificial lighting or photoperiodic treatments were conducted. Plants were germinated at 8° C. in calcareous soil.

Color reference are made to the Royal Horticultural Society Colour Chart (RHS), 2001 edition, except where general colors of ordinary significance are used. Color values were taken under daylight conditions in a greenhouse in Cambridge, England. The age of the plants of 'Shannon' described is about 245 days from sowing.

CLASSIFICATION;
Botanical: *Buglossoides arvensis* 'Shannon'
Germination: Approximately 14 to 21 days at 8° C.
Root Initiation: Approximately 10-14 days at approximately 6° C.
Root description: Tap root with short fibrous laterals. Grey-Brown in color, not accurately measured with RHS chart.
PLANT:
Growth Habit: Erect. Herbaceous, multiple stems from taproot, densely antrorse pubescent hairs appressed and angled.
Planting situation: Plants in the ground.
Age of plant described: 245 days from sowing.
Height: To top of foliage: 65 cm in standing crop
To top of flowers: 65 cm in standing crop.
Plant Spread: 25 cm in standing crop.
Growth Rate: Very slow over winter, vigorous in spring. Plant continues to grow during and after flowering.
Branching Characteristics:
Characteristics of Primary Lateral Branches:
Quantity: Numerous, influenced by stand density.
Diameter: 0.2-0.4 cm.
Length: 55-65 cm.
Color: RHS Yellow-Green 145B, Greyed-Red 178A where exposed.
Texture: Antrorse pubescent.
Strength: Stiff; thick-walled hollow cross section.
Internode length: 0.5 to 5 cm.
FOLIAGE:
Leaf: Simple, alternate, sessile, lanceolate to ovate, densely appressed pubescent on both surfaces with prominent mid rib below, entire.

Arrangement: Alternate.
Quantity: Approximately 5-10 per stem beneath the branch point, then 10 to 15 per inflorescence.
Average Length: True leaf 5.0 cm; bracts 3.0 cm; leaves continue to enlarge as plant grows.
Average Width: 1-1.2 cm.
Shape of blade: Lanceolate to ovate.
Apex: Round, acute.
Base: Tapering, cuneate, rounded.
Margin: Smooth, entire.
Texture of top surface: Rough.
Texture of bottom surface: Rough.
Pubescence: Pilose, standing at an angle.
Aspect: Bracts angled upwards but slightly curved towards tips; older leaves more horizontal and downward curve more pronounced.
Color:
   Young foliage upper side: RHS Yellow-Green 147A.
   Young foliage under side: RHS Yellow-Green 147B.
   Mature foliage upper side: RHS Yellow-Green 147B.
   Mature foliage under side: RHS Green 138A.
Venation:
   Type: Pinnate, conspicuous midrib on lower surface, secondary venation barely visible.
   Venation color upper side: RHS Yellow-Green 147B.
   Venation color under side: RHS Green 138D.
Petiole: Sessile.
INFLORESCENCE:
Natural flowering season: March to June; main flowering April to late May.
Days to flowering from seed: 170-185 days from mid-autumn sowing to first buds opening.
Inflorescence and flower type and habit: Polychasial cyme. Typically branching to three inflorescences (sometimes just two) with paired bracts and a flower at the branch, flowers and bracts alternate thereafter.
Rate of flower opening: 4 to 10 days from bud to fully opened flower.
Flower Longevity on Plant: About 7 days, depending on temperature/rainfall.
Persistent or Self-Cleaning: Self-cleaning.
Bud:
   Shape: Rounded.
   Length: 0.3 cm.
   Diameter: 0.1 cm.
   Color: RHS White 155A.
Flower size:
   Diameter: 0.2 cm.
   Length: 0.4 cm.
Petals:
   Length: 0.2 cm.
   Diameter: 0.1 cm.
   Quantity: 5.
   Texture: Smooth.
   Apex: Round, obtuse.
   Color:
      When opening:
      Upper surface: RHS White 155A.
      Lower surface: RHS White 155A.
      Fully opened:
      Upper surface: RHS White 155A.
      Lower surface: RHS White 155A.
      Ageing/Fading:
      Upper surface: RHS White 155D.
      Lower surface: RHS White 155D.
Floral Tube:
   Length: 0.3-0.4 cm.
   Diameter: 0.1 cm.
   Texture:
      Inner: Pubescent.
      Outer: Pubescent.
   Color:
      When opening:
         Inner surface: Top of tube RHS White 155A. Base of tube Greyed-Green 189B.
         Outer surface: Top of tube RHS White 155A. Base of tube Greyed-Green 189B.
      Fully opened:
         Inner surface: Top of tube RHS White 155A. Base of tube Greyed-Green 189B.
         Outer surface: Top of tube RHS White 155A. Base of tube Greyed-Green 189B.
      Ageing/Fading:
         Inner surface: Top of tube RHS White 155A. Base of Greyed-Green 189 B.
         Outer surface: Top of tube RHS White 155A. Base of tube Greyed-Green 189 B.
Sepals:
   Quantity per flower: 5.
   Shape: Linear, acuminate.
   Length: 0.6 cm.
   Width: 0.1 cm.
   Apex: Pointed acuminate.
   Base: Cuneate.
   Margin: Smooth, entire.
   Texture: Pubescent.
   Color: RHS Green 137A.
Peduncle:
   Length: 3.5-6.5 cm. from origin to first bract/flower; 1-4 cm internodes between successive bracts/flowers.
   Color: RHS Green 137B.
   Strength: Strong —becomes woody as seeds ripen. Thick-walled hollow cross section.
   Angle: Straight and almost vertical.
Pedicel:
   Length: 0.2-0.4 cm.
   Diameter: 0.2cm.
   Color: RHS Green 137B.
Fragrance: None observed.
REPRODUCTIVE ORGANS:
Stamens:
   Number: 5.
   Filament length: Less than 0.1 mm.
Anthers:
   Shape: Dorsifixed, parallel sacks with a groove between.
   Length: 0.1 mm.
   Color: RHS Greyed-Yellow 161 (too small to exactly specify under normal light).
Pollen:
   Color: RHS White NN155 (too small to specify under normal light.
   Quantity: Substantial.
Pistil:
   Number: 1.
   Length: 0.1 cm.
   Style:
   Length: Between 0.05 and 0.1 cm.
   Color: RHS Greyed-Green (too small to specify under normal light).
Stigma:
   Shape: Lobed.
   Color: RHS Greyed-Green (too small to specify under normal light).

SEED/FRUIT: Seeds borne in clusters of four. Thousand seed weight approx. 5.1 g; seed oil content approximately 22%; stearidonic acid 18%

DISEASE/PEST RESISTANCE: Good resistance to vertebrate pests, some susceptibility to powdery mildew during late season under stress conditions.

TEMPERATURE TOLERANCE: From expanded cotyledon stage, tolerates temperatures of minus −5° C.

I claim:

1. A *Buglossoides arvensis* plant named 'Shannon', representative seed deposited at the NCIMB in Aberdeen, Scotland and accorded International Depository Authority Accession No. NCIMB-43565.

2. A *Buglossoides arvensis* seed that produces the *Buglossoides arvensis* plant of claim 1.

3. A plant part obtained from the *Buglossoides arvensis* plant of claim 1.

4. A method of producing *Buglossoides arvensis* progeny comprising the steps of (a) crossing the plant *Buglossoides arvensis* 'Shannon', representative seed deposited at the NCIMB and accorded International Depository Authority Accession No. NCIMB-43565, as a female or male parent with another *Buglossoides arvensis* plant, and (b) selecting progeny.

5. The method according to claim 4, wherein the second *Buglossoides arvensis* plant is 'Shannon', representative seed deposited at the NCIMB and accorded International Depository Authority Accession No. NCIMB-43565.

\* \* \* \* \*